United States Patent
Fujiki et al.

(10) Patent No.: US 6,878,801 B2
(45) Date of Patent: Apr. 12, 2005

(54) OPTICALLY ACTIVE POLYTHIOPHENES

(75) Inventors: Michiya Fujiki, Kanagawa (JP); Hiroshi Nakashima, Kanagawa (JP); Julian R. Koe, Kanagawa (JP); Masao Morita, Kanagawa (JP); Hiromi Tamoto, Kanagawa (JP)

(73) Assignees: Japan Science and Technology, Saitama (JP); Nippon Telegraph and Telephone Corporation, Tokyo (JP)

(*) Notice: Subject to any disclaimer, the term of this patent is extended or adjusted under 35 U.S.C. 154(b) by 79 days.

(21) Appl. No.: 10/337,845

(22) Filed: Jan. 8, 2003

(65) Prior Publication Data

US 2003/0135021 A1 Jul. 17, 2003

Related U.S. Application Data (63) Continuation of application No. 09/700,115, filed as application No. PCT/JP00/00851 on Feb. 16, 2000, now abandoned.

(30) Foreign Application Priority Data

Mar. 11, 1999 (JP) .......................................... 11-065693

(51) Int. Cl.$^7$ ...................... C08G 75/00; C07D 333/10
(52) U.S. Cl. ...................... 528/380; 526/256; 549/59; 549/80; 549/83; 549/86
(58) Field of Search ...................... 528/380; 526/256; 549/59, 80, 83, 86

(56) References Cited

FOREIGN PATENT DOCUMENTS

JP          10-048678          2/1998

OTHER PUBLICATIONS

Fujiki et al., *Polymer Preprints*, 40(1), pp. 523–524, (1999).
Kotkar et al., *Frontiers of Polymer Research*, pp. 407–411, (1991).
Kotkar et al., *Journal Chemical Society Chemical Communications*, pp. 917–918, (1988).

*Primary Examiner*—David J. Buttner
(74) *Attorney, Agent, or Firm*—Wenderoth, Lind & Ponack, L.L.P.

(57) ABSTRACT

Novel polythiophenes which exhibit strong main chain absorption in the ultraviolet to visible region, show optical activity depending on the polymeric chain alone, and comprise as repeating units thiophene rings containing chiral substituent groups, and are represented by the following general formula:

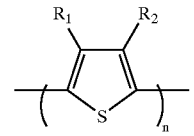

(wherein $R_1$ and $R_2$ are the same or different, each representing a hydrogen atom or an organic group, of which at least one is an enantiopure alkyl group with a branch structure at the β-position, and n represents the number of repeating units selected from 10 to 100,000).

8 Claims, 9 Drawing Sheets

OPTICALLY ACTIVE POLYTHIOPHENES

This is continuation of Ser. No. 09/700,115, filed Dec. 26, 2000 now abandoned which is a 371 of PCT/JP00/00851, filed Feb. 16, 2000.

TECHNICAL FIELD

The present invention concerns optically active polythiophenes. More specifically, the present invention concerns novel optically active polythiophenes useful as functional polymers such as polymeric semiconductors, polymeric conductors, electrochromic materials, electroluminescent materials, and nonlinear optical materials.

BACKGROUND ART

In recent years attention has been focused on polythiophenes as functional polymer materials, and studies directed towards the application of such materials as polymeric semiconductors, polymeric conductors, electrochromic materials, electroluminescent materials, and nonlinear optical materials have been reported. These conventional polythiophenes have absorption bands in the visible region of about 450 to 600 nm based on the π-conjugated main chain.

However, in practice, a broader absorption band is desirable, and in this sense the characteristics of conventional polythiophenes have had their limits. For example, to apply polythiophenes as luminescent materials, the absorption band related to the main chain should cover a broad region from ultraviolet to near infrared.

On the other hand, polymers such as poly(diphenylpyridylmethylmethacrylate), synthesized using sparteine-butyllithium as an initiator (e.g. Y. Okamoto et al., J. Am. Chem. Soc., 103, 6971 (1981)), whose main chain construct a one-directional helix are known as polymer materials which recognize enantiomers. These organic polymers having one-directional helices are actually on the market, as column materials for high-performance liquid chromatography, supported on the surface of silica gel, which allows the separation and analysis of optical isomers (Daicel Chemical Industries, Ltd., Chiralpak-OT and Chiralpak-OP).

However, these poly(triphenylmethylmethacrylate)-based materials have a serious disadvantage, in that they lose their enantiomer recognition ability once the side-chain section which fix the main chain helices are released. Hence, if characteristics such as the high resistance to hydrolysis and solvolysis of the helical main chain and the hydrocarbon side chains could be utilized, polythiophenes may be applied as column materials for high-performance liquid chromatography (HPLC) and gas chromatography (GC) which are performed under dark deoxygenated conditions. That is, these materials may be expected to show resistance when used repeatedly for a long period of time.

Also, most column materials presently used for enantiomer recognition, which can be used in separation and analysis by HPLC under reversed phase conditions, are those derived from biological substances most of which are alkyl derivatives containing amide bonds, causing them to deteriorate by hydrolysis. If column materials could be derived from thiophene-based materials containing optically active substituents, or if optically active polythiophenes with helices in the main chain could be supported on carriers, new uses of such materials as column materials for HPLC and GC may be developed.

However, contrary to such anticipations, polythiophenes showing the required performances described above have not been known so far.

The present invention has been carried out under the above circumstances, and its objective is to overcome the limits of conventional technology, to provide novel optically active polythiophenes with strong absorption characteristics due to the main chain in the ultraviolet to visible region, particularly those which exhibit strong main chain absorption characteristics in the ultraviolet-visible region, in solutions at room temperature, and show optical activity by itself, and thiophene monomers which provide such optically active polythiophenes.

DISCLOSURE OF INVENTION

In order to accomplish the above objectives, the present invention provides, firstly, an optically active polythiophene comprising, as repeating units, thiophene rings containing chiral substituent groups of the following formula

(wherein $R_1$ and $R_2$ may be the same or different, each representing a hydrogen atom or an organic group, of which at least one represents an enantiopure alkyl group with a branched-structure at the β-position, and n is a number chosen from 10 to 100,000 which repeats the number of repeating units).

Also, the present invention secondly provides, in reference to the first invention, optically active polythiophenes of the following formulas (A) and (B)

(wherein $R_1$ represents a hydrogen atom or an organic group) comprising as an enantiopure chiral substituent group, a (S)-2-methyloctyl group or a (R)-2-methyloctyl group.

Further, the present invention provides, thirdly, an optically active polythiophene represented by the following formulas (A1) and (B1)

A1

B1

Fourthly, optically active polythiophenes represented by the following formulas (A2) and (B2)

A2

-continued

B2 are provided.

Fifthly, the invention provides optically active polythiophenes represented by the following formulas (A3) and (B3)

A3

B3

Furthermore, the present invention provides, as a monomer which provides the polythiophenes of the first to fifth invention, optically active thiophenes of the following formula (wherein $R_1$ and $R_2$ are the same or different, each representing a hydrogen atom or an organic group, of which at least one represents an enantiopure alkyl group having a branched-structure at the β-position, and n is a number chosen from 10 to 100,000 which represents the number of repeating units) as the sixth invention.

In reference to the sixth invention, seventhly, the invention provides optically active thiophenes, containing as enantiopure chiral substituent groups a (S)-2-methyloctyl group or a (R)-2-methyloctyl group, represented by either one of the following formulas (A4) and (B4)

A4

B4

(wherein $R_1$ represents a hydrogen atom or an organic group)

Eighthly, the present invention provides optically active thiophenes represented by the following formulas (A5) and (B5)

A5

B5

Ninthly, the invention provides optically active thiophenes represented by the following formulas (A6) and (B6)

A6

B6

And tenthly, the invention provides optically active thiophenes represented by the following formulas (A7) and (B7):

A7

B7

BEST MODE FOR CARRYING OUT THE INVENTION

The present invention provides thiophene homopolymers which contain chiral alkyl groups comprising a branch-structure at the β-position, and thiophene monomers which contain chiral alkyl groups having a branch-structure at the β-position and provide the homopolymers described above. Embodiments are further illustrated below.

In the optically active polythiophenes and the optically active thiophenes which are monomers of such polythiophenes, at least one of the signs R$_1$ and R$_2$ is an enantiopure alkyl group comprising a branch-structure at the β-position. Examples of such β-branched alkyl groups may include various groups such as (S)-2-methylbutyl group, (S)-2-methyloctyl group, (S)-2-ethylhexyl group, (S)-2-ethyloctyl group, (R)-2-methylbutyl group, (R)-2-methyloctyl group, (R)-2-ethylhexyl group, and (R)-2-ethyloctyl group.

The other sign R$_1$ or R$_2$ which is not an enantiopure alkyl group may be a hydrogen atom or an organic group. The organic group may similarly be an enantiopure alkyl group with a branch-structure at the β-position. Examples of other organic groups include hydrocarbon groups that may comprise substituent groups. Embodiments may be alkyl groups such as methyl group, ethyl group, propyl group, and butyl group. These hydrocarbon groups may also contain a variety of functional groups.

More concretely, the optically active polythiophenes of the present invention include those represented by the formulas (A), (A1), (A2) and (A3) and (B), (B1), (B2) and (B3) described above. The monomers producing these optically active polythiophenes include those represented by the formulas (A4), (A5), (A6), and (A7) and (B4), (B5), (B6), and (B7) described above.

For the optically active polythiophenes of the present invention, monomers may be produced by deriving chiral alkyl halides from commercially available chiral alcohols having structures corresponding to the β-branched alkyl groups mentioned above, which may be further derived to provide optically active alkyl-substituted thiophenes.

To polymerize these monomers, the branch point at the β-position prevent racemization and rearrangement during oxidative condensation reaction. In addition, because the steric hindrance between monomers during condensation reaction is comparatively small, optically active polythiophene chains with high molecular weights may be easily produced. The present inventors have found that polythiophene main chains with β-chiral carbons, particularly β-branched chiral alkyl groups, and more preferably for its solubility, a (S)-2-methyloctyl group, prove effective in providing optically active polythiophenes in which the direction of the helices is biased to one direction.

In the present invention, by selecting proper substituent groups for the side chains R$_1$ and R$_2$, fundamental substances suitable for the studies of basic optical and electrical properties of ideal one-dimensional semiconductors and quantum small wire structures with no chain interaction as in conventional optically active polythiophenes may be provided. In addition, the optically active polythiophenes of the present invention may also be used as a new type of enantiomer-recognizing material.

The number of repeating units (n) in the above general formulas may be 10 to 100,000 in the present invention.

The embodiments of the invention are further illustrated by the following examples. Of course, the following examples are not to be construed as limiting the invention.

EXAMPLES
Synthesis of Substituted Thiophenes

Example 1

Bis[3,4-(S)-2-methyloctyl]thiophene 30 g of (S)-2-methyloctyl bromide and 4.2 g of magnesium were reacted in 120 ml dry ether to obtain a Grignard reagent. 2.0 g of nickel(0)bis-(diphenylphosphinopropane) dichloride were added to the reagent solution and 17 g of 3,4-dibromothiopene was slowly added dropwise to the solution at 40° C. After reaction for a total of 6 hours, the resulting product was decomposed by treatment with dilute hydrochloric acid, washed repeatedly with brine, and neutralized to obtain the title compound in a yield of 5.0 grams (21%). B.p. 152–165° C./0.8 mmHg; [α]D (24° C., neat) 5.79°; $^{13}$C-NMR (CDCl$_3$, 30° C.) 141.019, 120.838, 37.146, 36.575, 33.581, 31.960, 29.629, 27.193, 22.713, 19.767, and 14.124 ppm.

Example 2

3-Methyl-4-(S)-2-methyloctylthiophene 8.3 g of (S)-2-methyloctyl bromide and 1.2 g of magnesium were reacted in 25 ml dry ether to prepare a Grignard reagent. 0.50 g of Nickel (0)bis-(diphenylphosphinopropane)dichloride was added to the reagent solution and 5.9 g of 3-methyl-4-bromothiophene was slowly added dropwise to the solution at 40° C. After reacting for 6 hours in total, the product obtained was decomposed by treatment with water and dilute hydrochloric acid, washed repeatedly with brine, and then neutralized to obtain the title compound in a yield of 4.0 grams (54%). B.p. 101–106° C./1.0 mmHg; [α]D (24° C., neat) –0.02°; $^{13}$C-NMR (CDCl$_3$, 30° C.) 141.115, 137.197, 121.108, 120.694, 37.059, 36.675, 33.446, 31.960, 29.633, 27.154, 22.717, 19.684, 14.655, and 14.128 ppm.

Example 3

3-(S)-2-Methyloctylthiophene 21 g of (S)-2-methyloctyl bromide and 2.7 g of magnesium were reacted in 75 ml of dry ether to prepare a Grignard reagent. The reagent was slowly added dropwise in 100 ml of a tetrahydrofuran solution of 0.40 g of nickel(0)bis (diphenyl phosphinopropane)dichloride and 13.0 g of 3-bromothiophene at 40° C. After reaction for a total of 6 hours, the reaction product was decomposed by treatment with water and dilute hydrochloric acid, washed repeatedly with brine, and neutralized to obtain the title compound in a yield of 9.1 g (54%). Bp 101–106° C./1.0 mmHg; [α]D (24° C., neat) –0.05°; $^{13}$C-NMR (CDCl$_3$, 30° C.) 141.851, 128.739, 124.790, 120.659, 37.904, 36.732, 34.374, 32.013, 31.960, 29.616, 27.119, 22.713, 19.588, and 14.124 ppm.
Synthesis of Optically Active Polythiophenes

Example 4

Poly[bis{3,4-(S)-2-methyloctyl}thiophene]

After thoroughly drying, degassing, and substituting the inside of a reaction vessel by argon gas, a solution of 1.68 g of bis[3,4-(S)-2-methyloctyl]thiophene in 10 ml chloroform was added dropwise to a solution of 3.3 g of ferric chloride in 50 ml of chloroform, and stirred at room temperature for three days. The reaction mixture was dissolved in chloroform and reduced with an aqueous hydrazine. Solvents were removed in vacuum and the residue was washed with acetone for two days while heating. The title polymer was obtained in a yield of 1.02 g (60%) The weight-average molecular weight thereof was 19,500 and the number-average molecular weight thereof was 8400.

Figure 1:
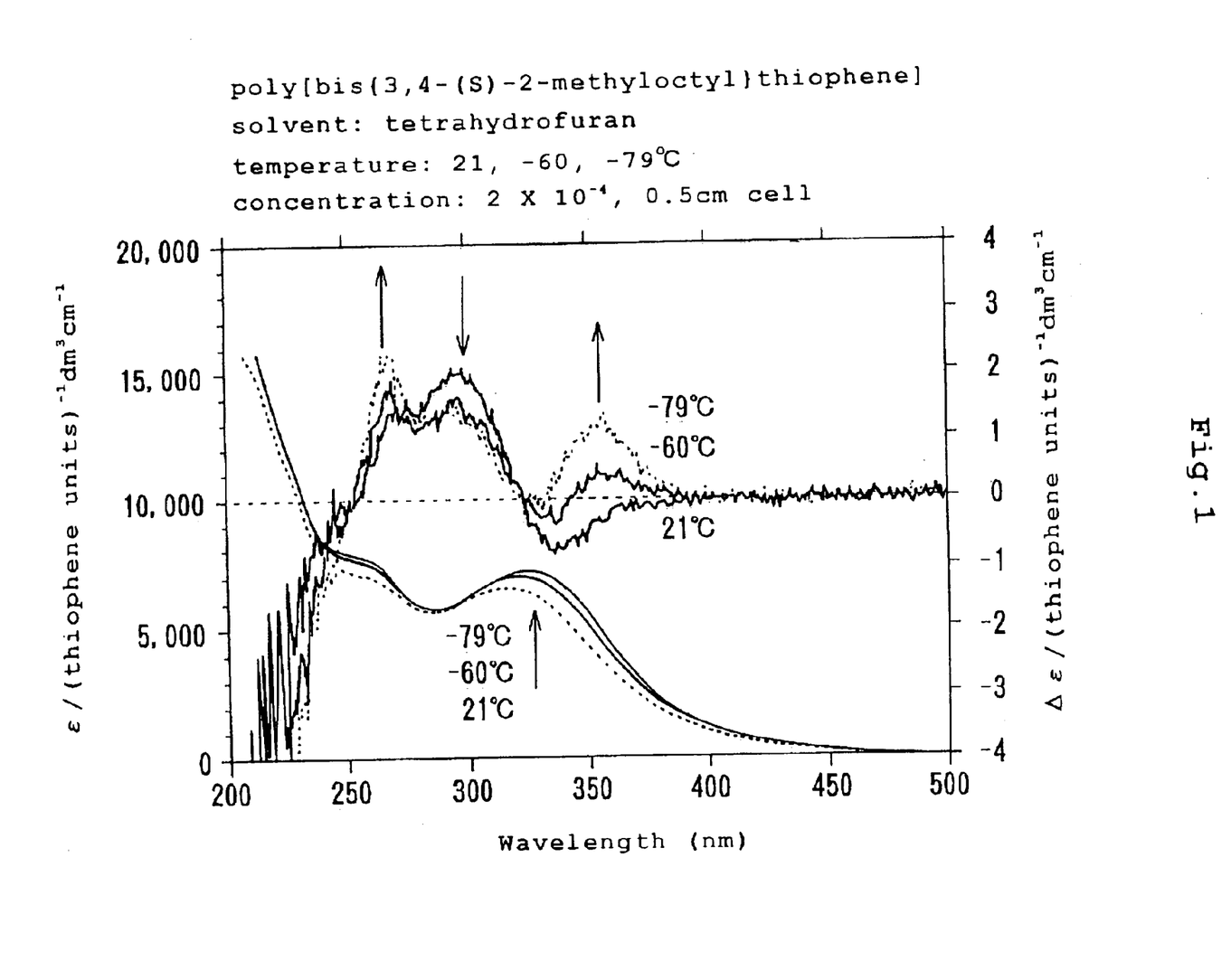
FIG. 1 shows the ultraviolet-visible absorption spectrum and the circular dichroism spectrum (in tetrahydrofuran. 21, −60; and −79° C.) of poly[bis{3,4-(S)-2-methyloctyl}thiophene] prepared in Example 4.

FIG. 1 shows the ultraviolet-visible absorption spectrum and the circular dichroism spectrum (in tetrahydrofuran, 21, –60, and –79° C.) of poly[bis{3,4-(S)-2-methyloctyl}thiophene] prepared in Example 4. In FIG. 1, the abscissa indicates the wavelength (nm), the left ordinate indicates the absorption coefficient [ε (thiophene repeating unit) $^{-1}$dm$^3$cm$^{-1}$], and the right ordinate indicates the circular dichroism absorption coefficient [Δε (thiophene repeating unit) $^{-1}$dm$^3$cm$^{-1}$].

Cotton absorption bands of 270 nm (positive), 300 nm (positive), and 340 nm (negative) were observed at 21° C. by comparing these spectra. The Cotton CD absorption band at the long wavelength side underwent red shift at –79° C. and at the same time the Cotton CD absorption was reversed to a positive sign. This was observed to be dependent on the helix-helix inversion.

Figure 2:
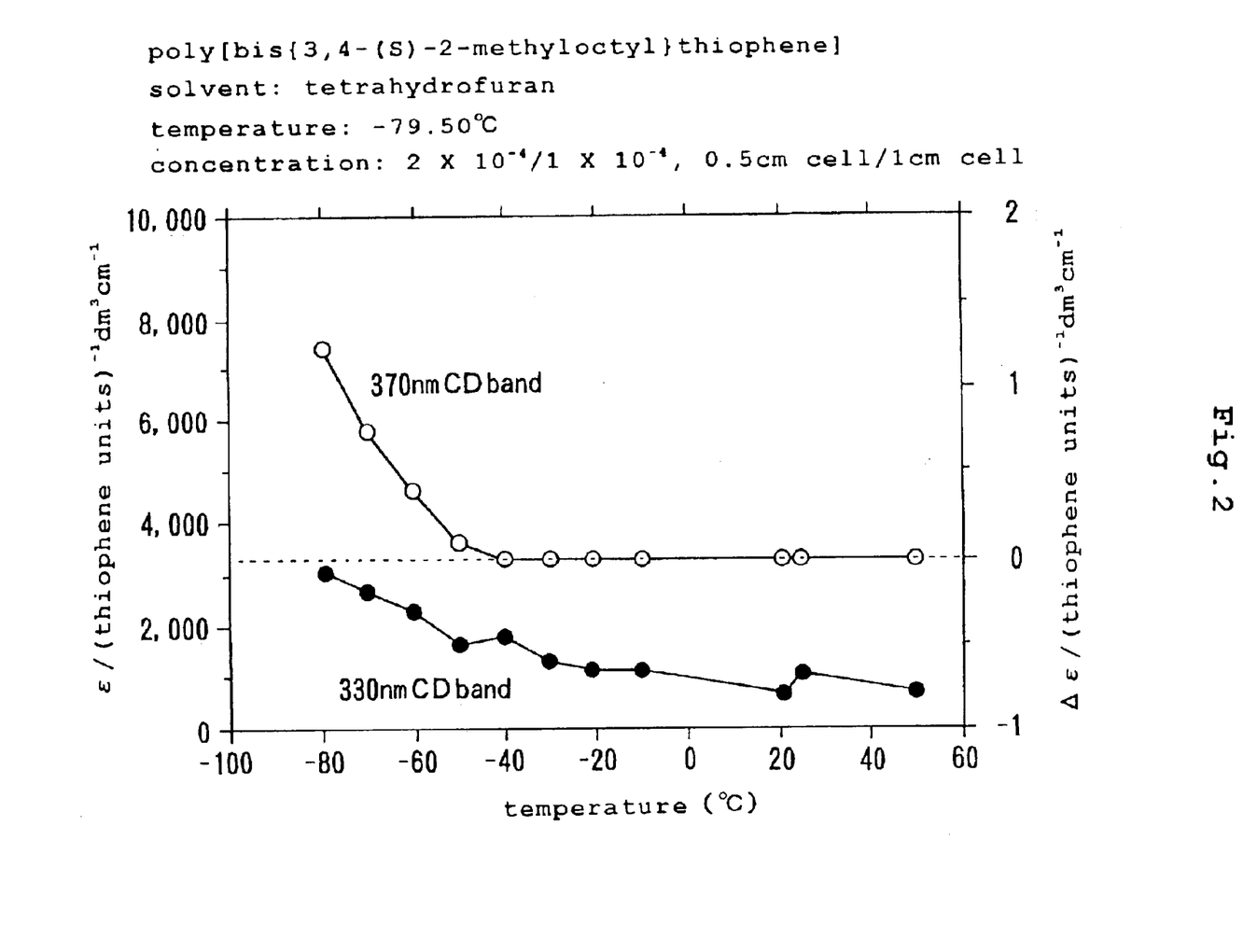
FIG. 2 shows the temperature dependence of negative Cotton CD absorption at 340 nm and positive Cotton CD absorption at 370 nm of the circular dichroism spectrum (in tetrahydrofuran) of poly[bis{3,4-(S)-2-methyloctyl}thiophene] prepared in Example 4.

FIG. 2 shows the temperature dependence of a negative Cotton CD absorption at 340 nm and a positive Cotton CD absorption at 370 nm. The figure reveals that at –60° C. a helix-helix inversion occurs. This change was reversible with the change in temperature.

Figure 3:
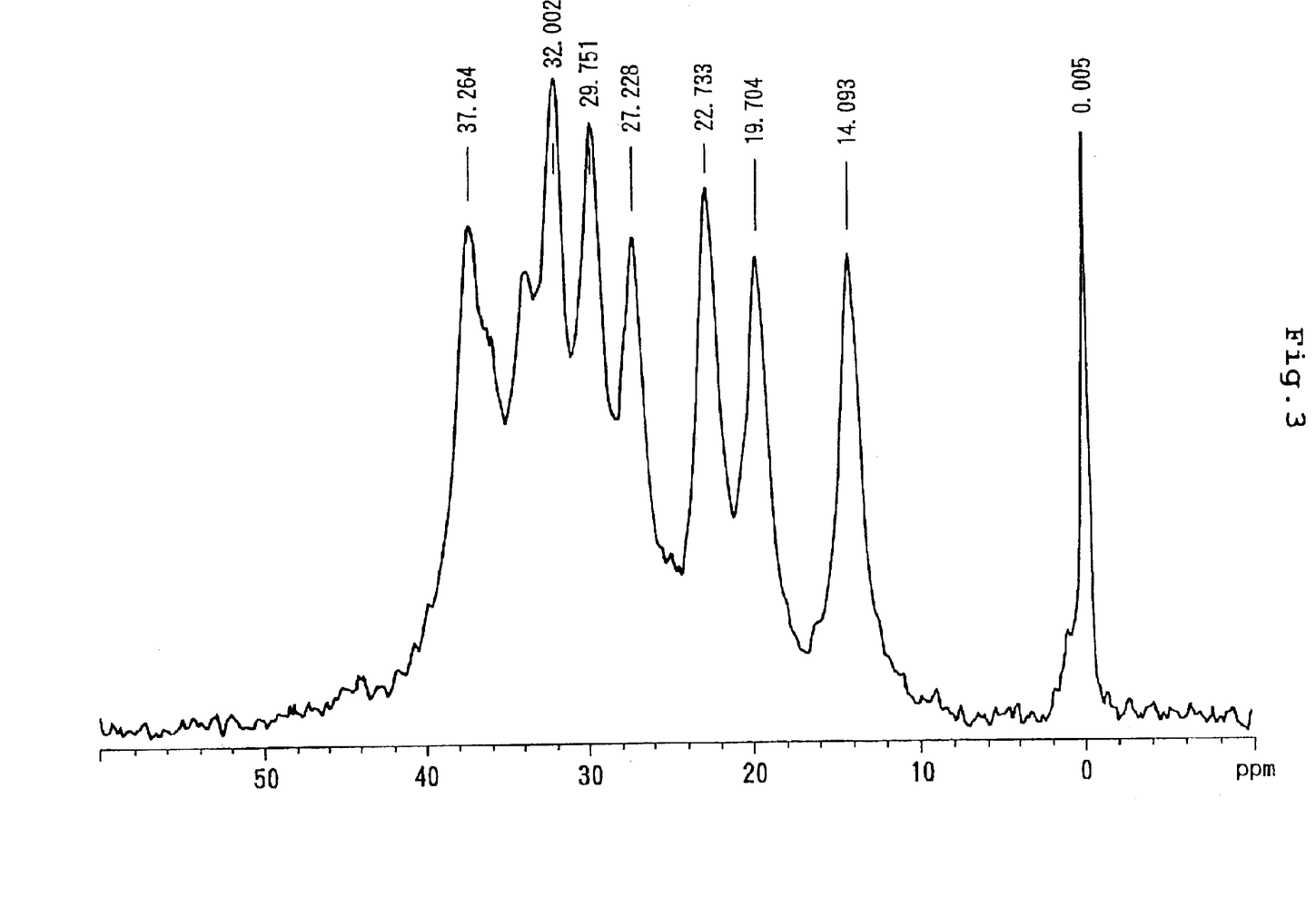
FIG. 3 shows the $^{13}$C-NMR spectrum (CDCl$_3$, 30° C.) of poly[bis{3,4-(S)-2-methyloctyl}thiophene] prepared in Example 4.
Figure 4:
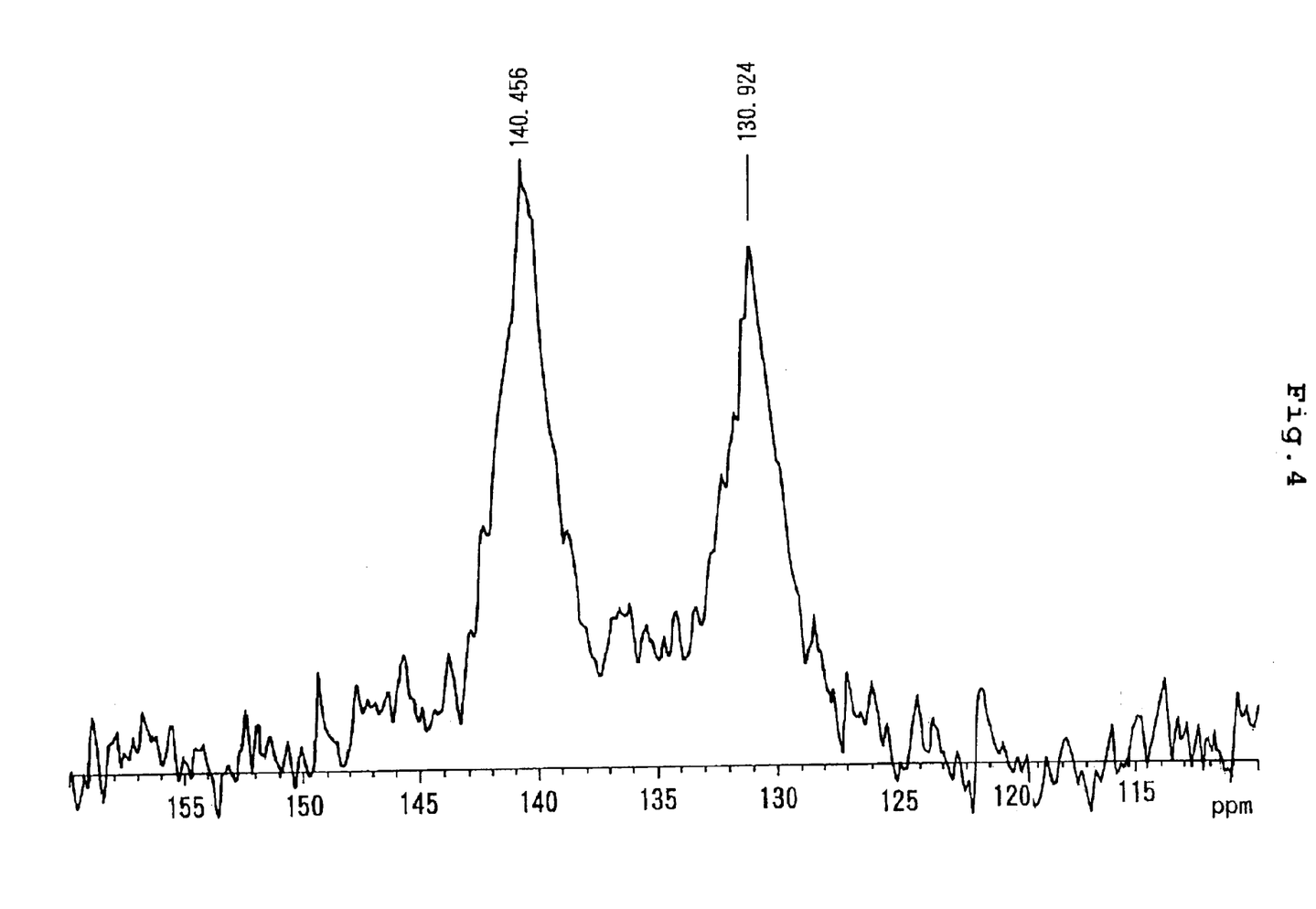
FIG. 4 shows the spectrum that follows FIG. 3.

FIG. 3 and FIG. 4 show the $^{13}$C-NMR spectra (CDCl$_3$, 30° C.).

Example 5

Poly[{3-methyl-4-(S)-2-methyloctyl}thiophene]

After thoroughly drying, degassing, and replacing the inside of a reaction vessel with argon gas, a solution of 0.9 g of [3-methyl-4-(S)-2-methyloctyl]thiophene in 10 ml of chloroform was added dropwise to a solution of 2.5 g of ferric chloride in 50 ml of chloroform and allowed to react with stirring at room temperature for one day. The reaction mixture solution was dissolved in chloroform and reduced with an aqueous hydrazine. Solvents were removed in vacuum and the residue was washed with acetone for two days while heating. The title polymer was obtained in a yield of 0.36 g (40%). The weight-average molecular weight was 107,000 and the number-average molecular weight was 3200.

Figure 5:
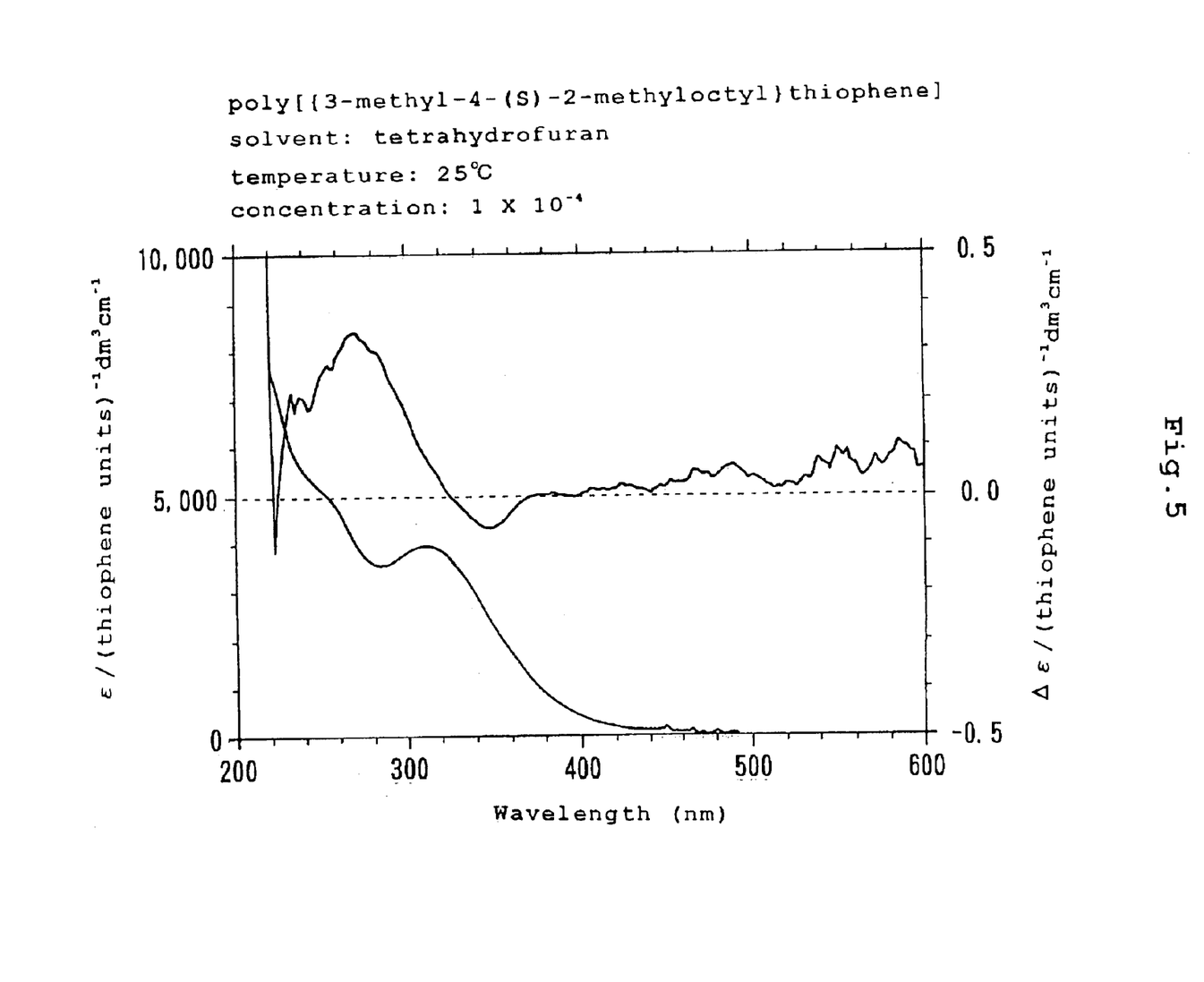
FIG. 5 shows the ultraviolet-visible absorption and the circular dichroism spectrum (in tetrahydrofuran, 25° C.) of poly[{3-methyl-4-(S)-2-methyloctyl}thiophene] prepared in Example 5.

FIG. 5 shows the ultraviolet-visible absorption spectrum and the circular dichroism spectrum (in tetrahydrofuran, 25° C.) of poly[{3-methyl-4-(S)-2-methyloctyl}thiophene] prepared in Example 5.

In FIG. 5 Cotton CD absorption bands of 270 nm (positive) and 350 nm (negative) were observed at 25° C.

Example 6

Poly[3-(S)-2-methyloctylthiophene]

After thoroughly drying, degassing, and replacing the inside of a reaction vessel with argon gas, a solution of 1.05 g of 3-(S)-2-methyloctylthiophene in 10 ml of chloroform was added dropwise to a solution of 1.9 g of ferric chloride in 50 ml of chloroform and stirred at room temperature for one day. The reaction mixture solution was dissolved in chloroform and reduced with an aqueous hydrazine. Solvents were removed in vacuum and the residue was washed with acetone for two days while heating. The title polymer was obtained in a yield of 0.32 g (31%). The weight-average molecular weight was 123,000 and the number-average molecular weight was 23,000.

Figure 6:
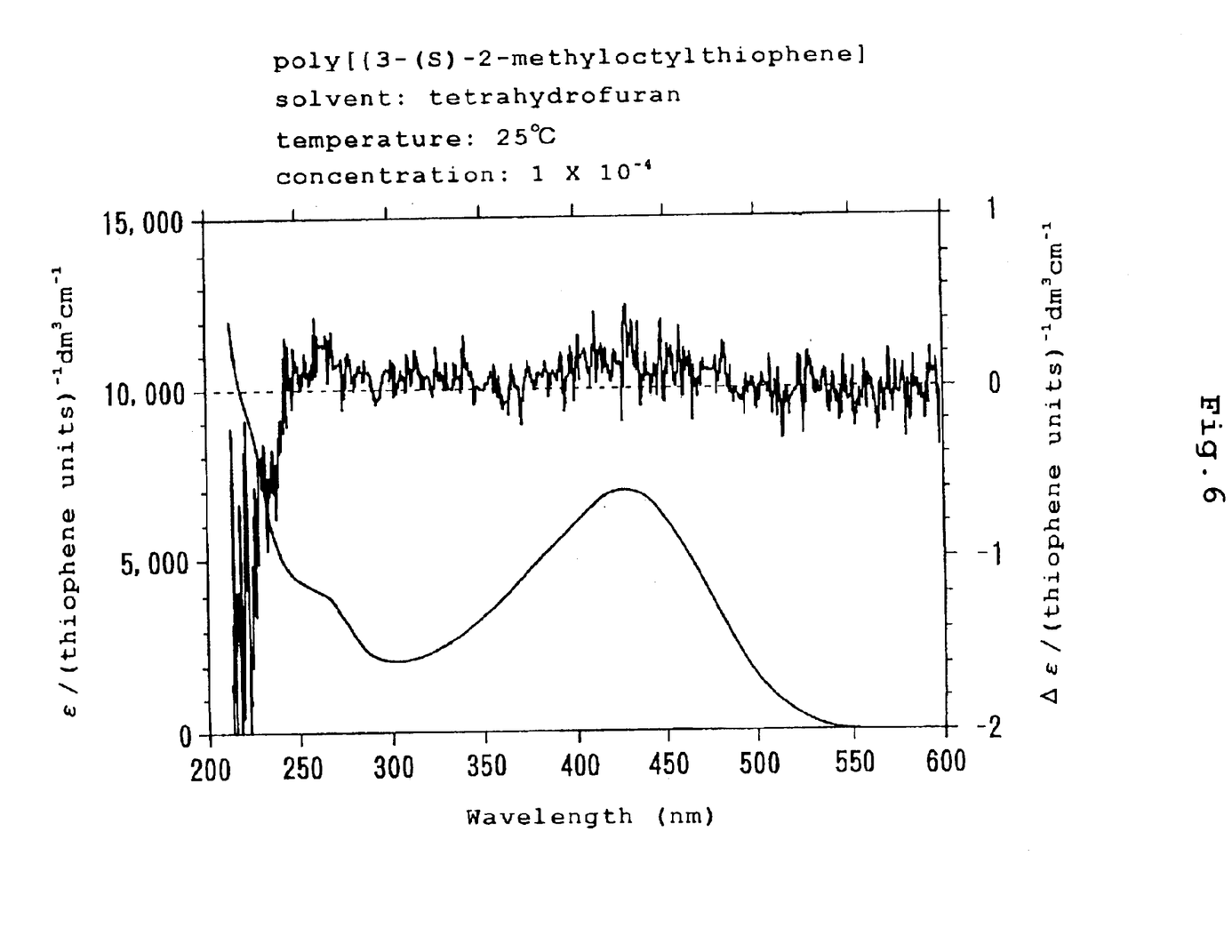
FIG. 6 shows the ultraviolet-visible absorption spectrum and the circular dichroism spectrum (in tetrahydrofuran, 25° C.) of poly[3-(S)-2-methyloctylthiophene] prepared in Example 6.

FIG. 6 shows the ultraviolet-visible spectrum and the circular dichroism spectrum (in tetrahydrofuran, 25° C.) of poly[3-(S)-2-methyloctylthiophene] prepared in Example 6.

FIG. 6 reveals that no Cotton CD absorption band is observed at 25° C.

Figure 7:
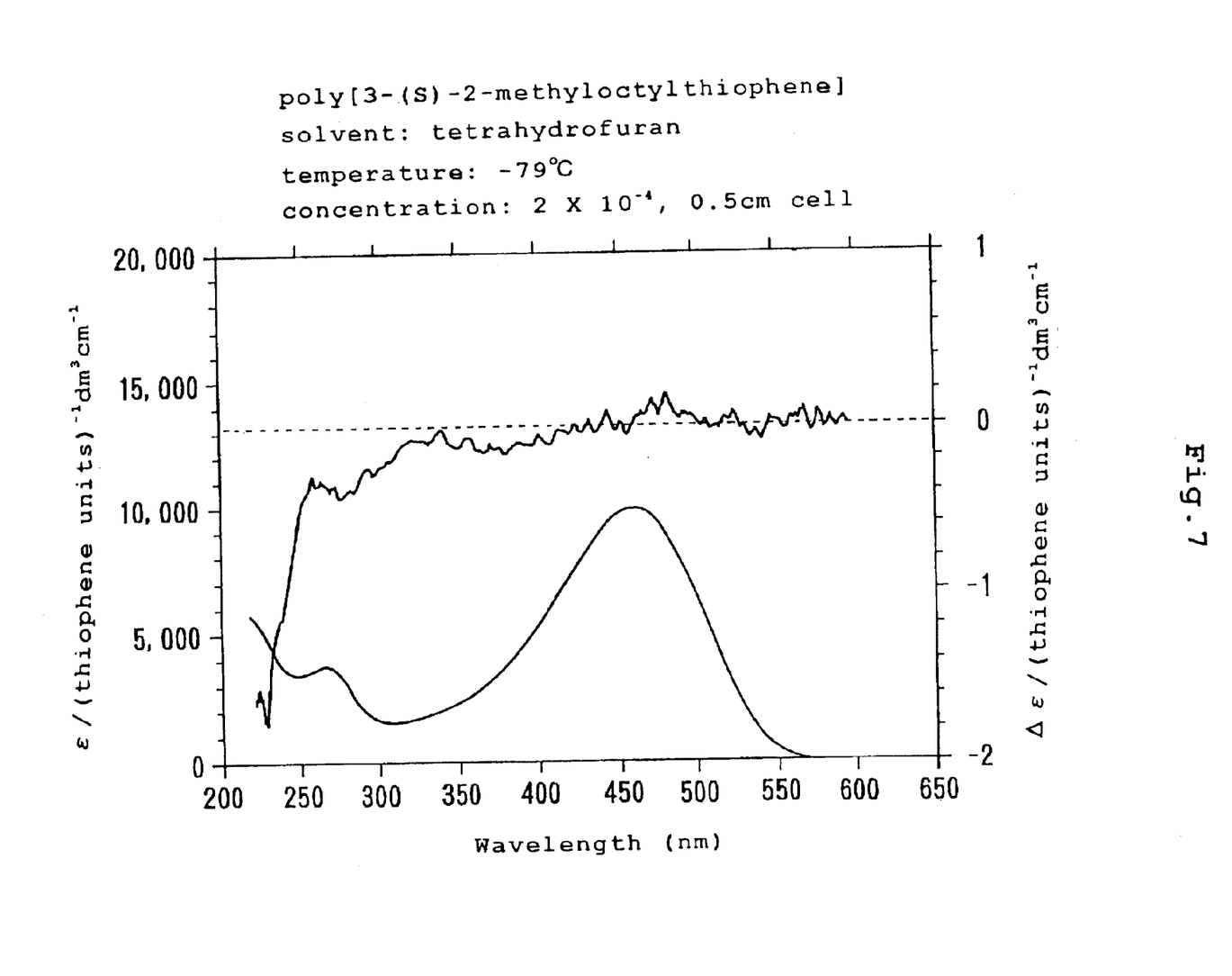
FIG. 7 shows the ultraviolet-visible absorption spectrum and the circular dichroism spectrum (in tetrahydrofuran, −79° C.) of poly[3-(S)-2-methyloctylthiophene] prepared in Example 6.

FIG. 7 shows the visible absorption spectrum and the circular dichroism spectrum (in tetrahydrofuran) at −78° C. Very weak Cotton CD absorption bands were observed at about 475 nm, about 380 nm, and about 270 nm as compared with the spectra for poly[bis{3,4-(S)-2-methyloctyl}thiophene] and poly[{3-methyl-4-(S)-2-methyloctyl}thiophene].

Figure 8:
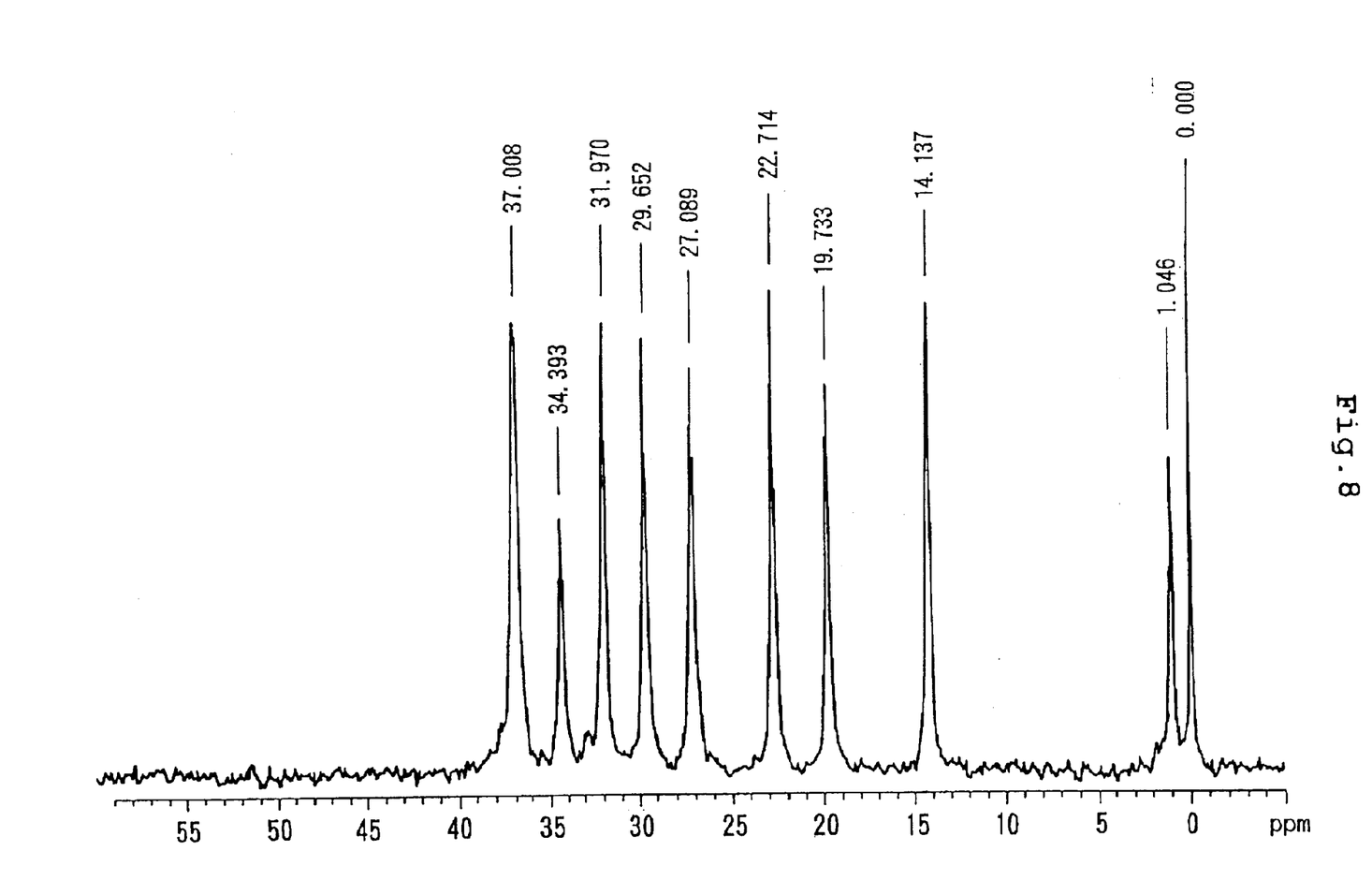
FIG. 8 is the $^{13}$C-NMR spectrum (CDCl$_3$, 30° C.) of poly[3-(S)-2-methyloctyl-thiophene] prepared in Example 6.
Figure 9:
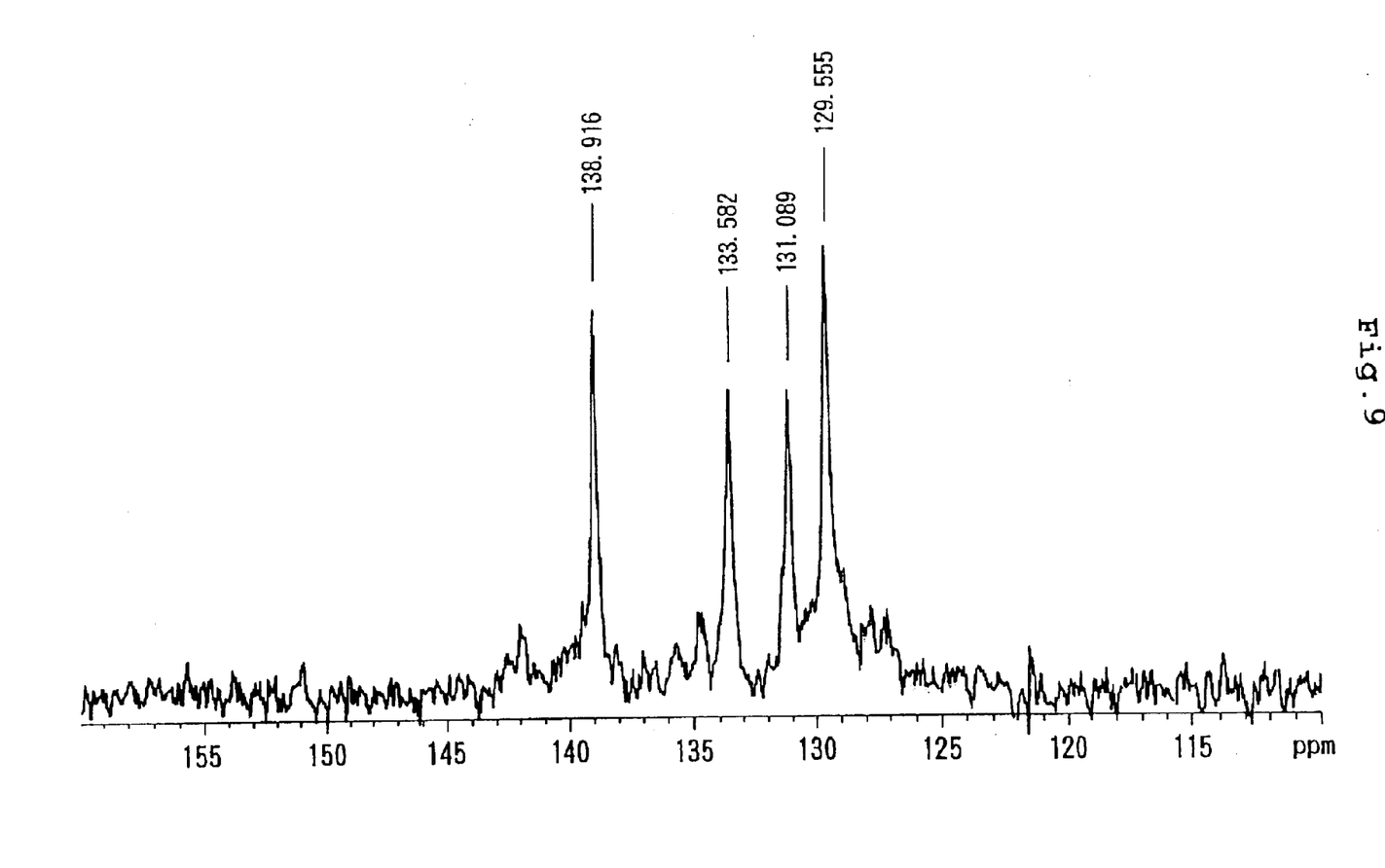
FIG. 9 shows the spectrum that follows FIG. 8.

FIG. 8 and FIG. 9 show the $^{13}$C-NMR spectra (CDCl$_3$, 30° C.).

Industrial Applicability

As illustrated above in detail, by using monomers comprising alkyl groups with branch-structures at the β-position, especially the three thiophene monomers comprising (S)-2-methyloctyl groups, the present invention easily provides a solvent-soluble optically active polythiophenes where the direction of the helices is oriented to one direction. Furthermore, by properly selecting side chain substituents, the optically active polythiophenes of the present invention may be extremely useful compared to conventional optically non-active polythiophenes, as fundamental model substances for the study of optical and electrical properties of ideal one-dimensional semiconductors with no interaction between chains, or of ultimate quantum small wire structure in an atomic level that may be realized in the near future. The polythiophenes of the present invention may be used as standard substances of polymers as well. These optically active polythiophenes may also be expected to serve as a new type of enantiomer-recognizing material.

What is claimed is:

1. Optically active polythiophenes comprising, as repeating units, thiophene rings with an (S)-2-methyloctyl group or an (R)-2-methyloctyl group, and represented by the following general formula:

A

B wherein R$_1$ represents a hydrogen atom or a 2-methyloctyl group and n represents the number of the repeating units selected from 10 to 100,000.

2. The polythiophenes of claim 1 represented by either one of the following formulas (A1) or (B1):

A1

B1

3. Polythiophenes represented by either one of the following formulas (A2) or (B2):

A2

B2

4. The polythiophenes of claim 1 represented by either one of the following formulas (A3) or (B3):

A3

B3

5. Optically active thiophenes comprising a (S)-2-methyloctyl group or a (R)-2-methyloctyl group, and represented by either of the following formulas (A4) or (B4):

A4

B4 wherein $R_1$ represents a hydrogen atom or a 2-methyloctyl group.

6. Optically active thiophenes represented by either of the following formulas (A5) or (B5):

A5

B5

7. Optically active thiophenes represented by either of the following formulas (A6) and (B6):

A6

B6

8. Optically active thiophenes represented by either of the following formulas (A7) or (B7):

A7

B7

* * * * *